United States Patent [19]

de Rooij

[11] Patent Number: 4,464,409

[45] Date of Patent: Aug. 7, 1984

[54] PROCESS FOR PREPARING 4-HYDROXY-5-METHYL-2,3-DIHYDROFURANONE-3 AND CHANGING ORGANOLEPTIC PROPERTIES OF FOODS

[75] Inventor: Johannes F. M. de Rooij, Maassluis, Netherlands

[73] Assignee: Lever Brothers Company, New York, N.Y.

[21] Appl. No.: 349,429

[22] Filed: Feb. 16, 1982

[30] Foreign Application Priority Data

Feb. 19, 1981 [NL] Netherlands .......................... 8100815

[51] Int. Cl.$^3$ ...................... A23L 1/226; A23L 1/231; C07D 307/60
[52] U.S. Cl. ..................................... 426/536; 549/477
[58] Field of Search ................. 549/477; 426/533, 536

[56] References Cited

U.S. PATENT DOCUMENTS

| | | | |
|---|---|---|---|
| 3,709,697 | 1/1973 | de Groot et al. | 426/536 X |
| 3,904,655 | 9/1975 | van den Ouweland et al. | 549/477 |
| 4,013,800 | 3/1977 | Shimazaki et al. | 426/536 |
| 4,045,487 | 8/1977 | Cleeland et al. | 549/477 X |
| 4,045,587 | 8/1977 | Katz et al. | 549/477 |

FOREIGN PATENT DOCUMENTS 910332 9/1972 Canada .

OTHER PUBLICATIONS

R. L. Whistler, M. L. Wolfrom and J. N. BeMiller "Methods in Carbohydrate Chemistry", vol. II, pp. 54-56, Academic Press Inc. New York, 1963.

Anderson, D. M. W. et al., "Talanta", 8, 605-611, (1961).
Anderson, D. M. W. et al., "J. Chem. Soc.", 1961, 5230-5234.
Nursten, H. E., "Food Chemistry", 6 (3), 263-277, (1981).
Votocek and Malachta in Coll. Czech. Chem. Communs 6, 241-250, (1934).
Peer, Van den Ouweland and DeGroot, Rec. Trav. Chim. Pays Bas 87, 1011-1016, (1968).
Peer and Van den Ouweland, Rec. Trav. Chim. Pays Bas 87, 1017-1020, (1968).
Hicks, Harris, Feather and Loeppky, J. Agric. Food Chem. 22(4), 724-725, (1974).

*Primary Examiner*—Richard Raymond
*Attorney, Agent, or Firm*—Amirali Y. Haidri; James J. Farrell

[57] ABSTRACT

4-Hydroxy-5-methyl-2,3-dihydrofuranone-3 is obtained by heating a solution with pH between 1 and 7 of a 5-keto-aldohexonic acid or a derivative thereof in a polar solvent at a temperature of 70° C. to 150° C. The 5-keto-aldohexonic acid is preferably 5-ketogluconic acid.

Meat flavors are obtained by heating the 5-keto-aldohexonic acid under the same conditions in the presence of a hydrogen sulphide donor like e.g. cysteine. This reaction product may be incorporated into foodstuffs. Also a process of modifying the organoleptic properties of a foodstuff or an ingredient for a foodstuff having a pH between 5 and 7 before consumption and which has to be heated at least 15 minutes to at least 70° C. by incorporating from 30 to 2000 ppm of a 5-keto-aldohexonic acid is described.

13 Claims, No Drawings

PROCESS FOR PREPARING 4-HYDROXY-5-METHYL-2,3-DIHYDRO-FURANONE-3 AND CHANGING ORGANOLEPTIC PROPERTIES OF FOODS

The present invention relates to a process of preparing 4-hydroxy-5-methyl-2,3-dihydrofuranone-3 from a 5-ketoaldohexonic acid or 5-aldulosonic acid, as well as to the 4-hydroxy-5-methyl-2,3-dihydrofuranone-3 (hereinafter also briefly called "the furanone") thus obtained.

The present invention also relates to a process for modifying the organoleptic properties of a foodstuff or an ingredient for a foodstuff which prior to consumption has a pH between 5 and 7 and has to be heated for at least 15 minutes at a temperature of at least 70° C., as well as to the foodstuffs or ingredients for foodstuffs thus obtained, and to a composition that is suitable to modify the organoleptic properties of a foodstuff or an ingredient for a foodstuff that prior to consumption has a pH between 5 and 7 and has to be heated for at least 15 minutes at a temperature of at least 70° C.

The synthesis of 4-hydroxy-5-methyl-2,3-dihydrofuranone-3 by reaction of aldopentoses with secondary amine salts has been described by Peer, Van den Ouweland and DeGroot in Rec. Trav. Chim. Pays Bas 87, 1011–1016 (1968); the synthesis thereof from D-ribose-5-phosphate has been described by Peer and Van den Ouweland in Rec. Trav. Chim. Pays Bas 87, 1017–1020 (1968) (cf. also Dutch Pat. Appln. No. 69 04058), and the formation from 1-dibenzyl-amino-1-desoxy-D-fructuronic acid has been described by Hicks, Harris, Feather and Loeppky in J.Agric.Food Chem. 22(4), 724–725 (1974).

It is also known, e.g. from Coll.Czech.Chem.Communs 6, 241–250 (1934), that the heating of an acidified (pH below 1) solution in water of 5-ketogluconic acid or D-xylo-5-hexulosonic acid invariably gives a substantially quantitative yield of 2-furaldehyde.

Finally it is stated in J.Chem.Soc. 1961, 5230–5234, that 93% pure calcium-L-sorburonate was decarboxylated to the extent of 98.3% in 69.4 hours by refluxing in deionised water. However, the suspension of calcium-L-sorburonate has a pH value above 7 and on heating decarboxylation takes place according to a different reaction mechanism.

At present, the commercially most readily available 5-ketoaldohexonic acid is the 5-ketogluconic acid, which can be simply obtained by oxidation of glucose with the aid of enzymes, nitric acid or bromine. The preparation of said acid has been described, inter alia, by Whistler, Wolfrom and Bemiller in "Methods in Carbohydrate Chemistry", Vol. II, Academic Press, New York, 1963, pp. 54–56.

It has now been found that if a solution of 5-ketoaldohexonic acid such as 5-ketogluconic acid, or a derivative thereof, such as a salt or an ester thereof, is heated in a polar medium with a pH between 1 and 7, a preferential conversion takes place into 4-hydroxy-5-methyl-2,3-dihydrofuranone-3. Although the Applicant does not want to be bound in any way to any theory, it is assumed that under the given circumstances the 5-keto-aldohexonic acid rearranges into the stable furanose-configuration, thus making the further favourable reaction possible.

The present invention therefore provides a process for the preparation of 4-hydroxy-5-methyl-2,3-dihydrofuranone-3, which is characterized in that a solution having a pH-value between 1 and 7 of a 5-keto-aldohexonic acid or 5-aldulosonic acid or a derivative thereof is heated in a polar solvent to a temperature of from 70° C. to 150° C.

The 5-keto-aldohexonic acid or 5-aldulosonic acid is preferably 5-ketogluconic acid or D-xylo-5-hexulosonic acid, but in this specification and the claims by a 5-keto-aldohexonic acid are also understood all possible optically active forms, or racemates of this acid, as well as all possible tautomeric forms (keto-enol tautomerism). Preferably, the 5-ketogluconic acid or D-xylo-5-hexulosonic acid (also called L-sorburonic acid) is used, but e.g. the D-arabino-5-hexulosonic acid or tagaturonic acid can also be used.

In the present specification and claims a derivative of a 5-keto-aldohexonic acid is understood to be a compound of the acid which under the reaction conditions can be converted into 4-hydroxy-5-methyl-2,3-dihydrofuranone-3 without any disturbing reactions taking place, such as organic or inorganic salts of the acid, e.g. an alkali metal or alkaline earth metal salt, or lower alkyl esters of the acid, such as e.g. the methyl or the ethyl ester. For use in foodstuffs preference is given to edible derivatives.

Since the 4-hydroxy-5-methyl-2,3-dihydrofuranone-3 is not very stable in a polar medium, part of the formed furanone is again decomposed, the decomposition also being due to the reaction with intermediate products, resulting in the formation of brown polymers.

At a pH of about 2.3 the degradation of the furanone is minimal and, consequently the yield optimal, but at a pH value of about 4 the furanose-configuration of the 5-keto-aldohexonic acid is most stable.

In the process according to the present invention a pH value ranging between about 2 and about 3 is preferred. The amount of acid compound required to impart to the reaction medium a pH between 1 and 7 is not particularly critical and may vary widely, but it has also been found that the reaction proceeds considerably better as the salt concentration or salt strength of the reaction medium is lower, and the salt concentration in the reaction medium should therefore be kept as low as possible.

Since the reaction is unimolecular and the degradation of the product is dependent on several molecules, the yield of the furanone is higher upon dilution. Hence in the process according to the invention the dilution of the reaction medium is important. In the case of an increased dilution there is also less degradation of the reaction product, which, of course, is very advantageous from an economical point of view. It will be evident that the practical limits will be set by economical considerations as regards the recovery of the polar solvent used and as regards isolation of the product. It has been found that in the case of strong dilutions one can still obtain acceptable yields of the desired furanone at a relatively high pH-value.

At reaction temperatures above about 150° C. the formation of 2-furaldehyde is promoted at the cost of the formation of the furanone, because at higher temperatures the stable furanose-configuration of the 5-keto-aldohexonic acid, such as the 5-keto-gluconic acid, is destroyed. At lower temperatures the reaction proceeds at economically less attractive velocities. In the process of the present invention preferably a temperature is used between about 95° C. and about 110° C., particular preference being given to a temperature between 100° C. and 105° C. There is of course a relation between the reaction temperature and the reaction time. For suitable reaction times in the order of 0.5 to 10 hours, preferably from 1 to 5 hours, the reaction is preferably carried out at boiling point at atmospheric pressure. However, if desired the reaction can also be carried out at increased pressure in a closed reactor, in which case, of course, the temperature can be variable. After completion of the reaction the reaction mixture is allowed to cool and the desired furanone can be isolated in a manner known per se. This can be effected, for example, by saturating the reaction mixture with sodium chloride after it has been cooled and extracting the mixture thus obtained several times with portions of a solvent. The combined organic layers are then dried and concentrated. Any undesirable contaminations can be removed from the impure product by recrystallisation.

It has also been found that the reaction does not or substantially does not proceed in a non-polar medium. For obvious reasons the polar medium is preferably water, but also other polar solvents, such as the lower aliphatic alcohols, e.g. methanol and ethanol, can be used, as well as mixtures thereof or mixtures with water.

The heating of the 5-keto-aldohexonic acid or its derivative can be carried out in the presence of a foodstuff or an ingredient for a foodstuff, while ensuring that said foodstuff or the ingredient therefor does not have such properties that the conversion of the 5-keto-aldohexonic acid into furanone is adversely affected.

It has additionally been found that if the heating of the 5-keto-aldohexonic acid or its derivative was carried out in the way described, but in the presence of a hydrogen sulphide donor, flavouring substances having a meat flavour were formed. In the specification and claims a hydrogen sulphide donor is understood to be hydrogen sulphide, in the form of a gas, a liquid or a solution, or an organic or inorganic compound capable of releasing hydrogen sulphide, either in the form of a gas or "in statu nascendi" under the conditions at which the reaction takes place.

Suitable examples of organic hydrogen sulphide donors are cysteine, or a cysteine-containing peptide, such as glutathione, cystine, mercaptoacetamide, thioacetamide or salts, e.g. potassium or sodium salts, hypochlorides, esters, or other single derivatives of these sulphur containing compounds.

Suitable examples of inorganic hydrogen sulphide donors are sulphides or hydrosulphides of alkali metals, alkaline earth metals or ammonia, such as sodium sulphide, potassium sulphide, ammonium sulphide, calcium sulphide or the corresponding hydrosulphides. Other inorganic metal sulphides, for example ferrosulphide, can also be used.

The reaction mixture containing the 5-keto-aldohexonic acid or its derivative and the hydrogen sulphide donor can optionally also contain other ingredients to improve or strengthen the character of the flavour ultimately to be obtained. These optional ingredients can be added before, during or after the reaction of the 5-keto-aldohexonic acid or its derivative and the hydrogen sulphide donor. Examples of such optional ingredients are amino acids, aliphatic $C_{12}$-$C_{18}$ fatty acids, for example palmitic acid or oleic acid, or a salt or ester, for example a glyceride thereof.

The present invention therefore also provides a process for modifying the organoleptic properties of a foodstuff or an ingredient for a foodstuff, which before consumption has a pH between 5 and 7 and has to be heated for at least 15 minutes at a temperature of at least 70° C., which is characterized in that a 5-keto-aldohexonic acid or a derivative thereof is incorporated together with a hydrogen sulphide donor into the foodstuff or the indient therefor.

The present invention also provides a process for modifying the organoleptic properties of a foodstuff or an ingredient for a foodstuff, which is characterized in that the reaction mixture, obtained on heating at 70°-150° C. at a pH value of 1 to 7 in a polar solvent of a 5-keto-aldehexonic acid or a derivative thereof and a hydrogen sulphide donor, is incorporated into the foodstuff or the ingredient therefor.

It has also been found that if a 5-keto-aldohexonic acid or 5-aldulosonic acid, such as e.g. 5-ketogluconic acid or D-xylo-5-hexulosonic acid or a derivative thereof, is incorporated into a foodstuff which before consumption has a pH of between 5 and 7 and has to be heated for at least 15 minutes at a temperature of at least 70° C., the organoleptic properties of the foodstuff, notably its odour and/or its flavour and/or its taste, are modified in a positive sense.

By the term "modify" is understood the imparting of odour, flavour and/or taste to a previously neutral, relatively tasteless foodstuff or an ingredient therefor, or the strengthening or improving of an existing odour, flavour and/or taste of a foodstuff or an ingredient for a foodstuff. By the term "foodstuff" or "ingredient for a foodstuff" is understood a solid or liquid, edible substance for humans or animals that mostly has a nutritional value.

The present invention thus also provides a process for modifying the organoleptic properties of a foodstuff or an ingredient for a foodstuff which before consumption has a pH of between 5 and 7 and has to be heated for at least 15 minutes at a temperature of at least 70° C., which is characterized in that a 5-keto-aldohexonic acid or a derivative thereof is incorporated into the foodstuff or the ingredient therefor. The 5-keto-aldohexonic acid used is preferably the 5-ketogluconic acid and the derivative is preferably an edible organic or inorganic salt, or a lower alkyl ester such as e.g. its methyl or ethyl ester.

The present invention also relates to foodstuffs or ingredients for foodstuffs obtained by means of the process according to the present invention.

The amount of 5-keto-aldohexonic acid that is incorporated into the foodstuff or the ingredient therefor with a pH of between 5 and 7, should be sufficient to impart the desired flavour- and/or taste characteristic thereto at the indicated heating thereof. The amount used varies depending on the type of foodstuff or ingredient therefor and depending on the intensity and the type of flavour and/or taste the foodstuff already has and the ultimately desired effect. Generally however, the amount of 5-keto-aldohexonic acid used ranges from 30 to 2000 parts per million, based on the weight of the foodstuff before heating for consumption. Preferably an amount of from 100 to 300 ppm of the 5-keto-aldohexonic acid is used in the foodstuff. If a derivative of the 5-keto-aldohexonic acid is used, the amount used is chosen such that the acid formed from this amount of derivative is from 30 to 2000 ppm, calculated on the amount of the foodstuff. The incorporation of the 5-keto-aldohexonic acid in the foodstuff or the ingredient therefor makes it possible to heat the foodstuff for a considerable time without any loss of flavour.

The present invention further relates to a composition suitable for modifying the organoleptic properties of a foodstuff or an ingredient therefor, which before consumption has a pH value between 5 and 7 and has to be heated for at least 15 minutes at a temperature of at least 70° C., which is characterized in that said composition comprises a 5-keto-aldohexonic acid or a derivative thereof. Of this composition, which is suitable for modifying the organoleptical properties of a foodstuff or an ingredient therefor, in practice such an amount is added to the foodstuff as to ensure that the 5-keto-aldohexonic acid is present in the final foodstuff before consumption in an amount of from 30 ppm to 2000 ppm, preferably from 100 ppm to 300 ppm, calculated on the weight of the foodstuff prior to the indicated heating before consumption.

Examples of foodstuffs in which the 5-keto-aldohexonic acid can be incorporated are soups, soup mixes, meats, sauces, gravies, meals, but also spreads and dressings, bakery products, dairy produce and the like.

The 5-keto-aldohexonic acid and/or its derivative can be incorporated in the foodstuff or the ingredient therefor together with one or more diluents or carriers. Suitable diluents are preferably edible alcohols, such as ethanol or propylene glycol; suitable carriers are gums, maltodextrins and similar substances. The 5-keto-aldohexonic acid and/or its derivative can be incorporated in the carrier by mixing or drying, such as freeze-drying, drum-drying or spray-drying. The 5-keto-aldohexonic acid and/or its derivative can also be included in the foodstuff in an encapsulated or coated form. The encapsulating or coating material is preferably an edible substance, such as fats or gums. The 5-keto-aldohexonic acid and/or its derivative can be incorporated in the foodstuff in the form of a solution, a dispersion or an emulsion.

In the composition according to the present invention, which is suitable for modifying the organoleptic properties of a foodstuff or an ingredient therefor, the 5-keto-aldohexonic acid and/or its derivative can be used together with other taste- or flavour-imparting substances, taste- or flavour-enhancing substances, colourants, stabilizers, thickeners, sweeteners, herbs, spices, antioxidants, surface-active substances and similar additives.

The invention will now be illustrated by means of the following examples, which are in no way to be regarded as limitative with respect to the scope of protection.

EXAMPLE 1

0.2 mmol (46.4 mg) of potassium 5-ketogluconate were dissolved in 4 ml of a 0.2 molar $KH_2PO_4$ buffer solution having a pH of 2.3, and this solution was heated to reflux by means of an oil bath with a temperature of 120° C. At suitable intervals 50 μl samples were drawn from the reaction mixture and injected into a high-pressure liquid chromatography column (Lichrosorb RP 18 (5μ) column of 25×4.6 mm). The column was eluated with a methanol/water mixture (7:1 vol/vol) at a rate of flow of 1 ml/min at ambient temperature. Retention time 7.2 min. The following yields of 4-hydroxy-5-methyl-2,3-dihydrofuranone-3 were obtained:

| Reaction time (h) | Yield (%) |
|---|---|
| 0.5 | 4.5 |
| 1 | 8.4 |
| 2 | 10.7 |
| 4 | 11.2 |
| 6 | 10.6 |

EXAMPLES 2–4

In the same way as described in Example 1 potassium-5-keto-gluconate was dissolved in a 0.2 molar $KH_2PO_4$ buffer solution with a pH of 2.3 and heated to reflux, using the following initial concentrations of potassium-5-ketogluconate:
200 mmol/l (Example 2); 100 mmol/l (Example 3) and 12.5 mmol/l (Example 4).

The following yields of 4-hydroxy-5-methyl-2,3-dihydrofuranone-3 were obtained:

| Reaction time (h) | Yield (%) | | |
|---|---|---|---|
| | Example 2 | Example 3 | Example 4 |
| 0.5 | 2.8 | 4.7 | 3.6 |
| 1 | 4.2 | 8.3 | 10.3 |
| 2 | 5.2 | 10.5 | 17.6 |
| 5 | 3.2 | 10.7 | 23.5 |
| 8 | — | — | 23.7 |

Taking the conditions of Example 3 as a reference, it may be concluded that an initial concentration of the 5-ketogluconate which is twice as high, results in a yield of furanone which is twice as low (Example 2). If, however, the ketogluconate is diluted eight times (Example 4), the maximum yield of furanone is more than twice as high.

EXAMPLES 5–7

In the same way as described in Example 1, but starting with 12.5 mmol/l of potassium-5-ketogluconate, the reaction was carried out at pH=1.6 (Example 5) and pH=1.0 (Example 6). The reaction was also carried out starting with 0.9 mmol/l of potassium-5-ketogluconate and at pH=5.7 (Example 7). The following yields of furanone were obtained:

| Reaction time (h) | Yield (%) | | |
|---|---|---|---|
| | Example 5 | Example 6 | Example 7 |
| 0.5 | 3.0 | 0.7 | 2.6 |
| 1 | 7.0 | 2.0 | 4.0 |
| 2 | 13.6 | 6.0 | 5.8 |
| 4 | 21.1 | 9.0 | 7.2 |
| 5 | 22.8 | 10.0 | 8.5 |
| 7 | 25.2 | 10.8 | — |

The yield of furanone at pH=1.6 is higher, as a result of the decreased degradation. From Example 7 it appears that at a lower initial concentration of the potassium-5-ketogluconate and a relatively high pH-value the reaction still gives a reasonable yield. At the pH-values of 1.0 and 1.6, however, the formation of 2-furaldehyde increased and after 8 hours' reaction 3.8% and 3.1%, respectively, of 2-furaldehyde had formed.

EXAMPLES 8–11

In the same way as described in Example 1, but starting with an initial concentration of 2.5 mmol/l of potassium-5-ketogluconate, the reaction was carried out at pH=1.6 (Example 8), pH=2.3 (Example 9), pH=2.9 (Example 10) and pH=3.5 (Example 11). The following yields of 4-hydroxy-5-methyl-2,3-dihydrofuranone-3 were obtained:

| Reaction time (h) | Yield (%) | | | |
|---|---|---|---|---|
| | Ex. 8 | Ex. 9 | Ex. 10 | Ex. 11 |
| 0.5 | 2.0 | 4.0 | 4.6 | 2.0 |
| 1 | 5.2 | 7.8 | 8.6 | 4.4 |
| 2 | 14.6 | 20.4 | 13.8 | 8.4 |
| 4 | 23.2 | 31.4 | 18.4 | 12.4 |
| 5 | 27.8 | 36.4 | 19.2 | 14.4 |
| 6 | 30.2 | 39.8 | 19.6 | 14.8 |
| 7 | 33.0 | — | 18.6 | 14.6 |

At this concentration of the potassium-5-ketogluconate the reaction velocity was at a maximum at pH=2.3. The maximum yield of furanone under these conditions was 39.8%.

EXAMPLE 12

In order to examine the effect of the salt strength or salt concentration of the reaction mixture, the potassium salt of the 5-ketogluconic acid was converted into the free acid by means of a Dowex cation-exchange-column in the H+-form. At a concentration of 2.5 mmol/l the 5-keto-gluconic acid in distilled water had a pH of 3.0. The pH-value of this solution was brought at 2.3 by the addition of concentrated phosphoric acid. The mixture thus obtained was heated to reflux as described in Example 1. The following yields of furanone were obtained:

| Reaction time (h) | Yield (%) |
|---|---|
| 0.5 | 1.7 |
| 1 | 5.7 |
| 2 | 16.0 |
| 4 | 29.7 |
| 5 | 34.8 |
| 6 | 39.3 |
| 7 | 41.3 |
| 8 | 44.5 |
| 10 | 47.3 |
| 15 | 49.5 |

It was found that if the reaction was carried out at 150° C., the formation of the furanone took place about 2.5 times as fast and with relatively less browning than when the reaction was performed at 100° C., but far more 2-furaldehyde was formed (the ratio of furanone to 2-furaldehyde was 1.8). If the 5-ketogluconic acid in iso-pentanol was heated at 100° C., no 4-hydroxy-5-methyl-2,3-dihydrofuranone-3 could be detected in the reaction mixture.

EXAMPLE 13

2 mmol (388 mg) of the free 5-ketogluconic acid was dissolved in 40 ml of distilled water and the solution was heated to reflux for 4.5 hours as described in Example 1. At the start of the reaction the pH was 2.4 and at the end of the reaction the pH was 2.5. After the reaction mixture had cooled, it was saturated with sodium chloride and extracted eight times with 20 ml of chloroform. The combined organic layers were dried over magnesium sulphate and concentrated in an evaporator (Rotavapor, ex Büchli, Switzerland). The product obtained (yield 15%) was an oil which solidified on standing. Recrystallisation from a diethylether/petroleum ether (40°–60°)-mixture (20/80 vol/vol, respectively) gave pure 4-hydroxy-5-methyl-2,3-dihydrofuranone-3 having a melting point of 126.5°–127.5° C.

EXAMPLE 14

A flavouring mixture used to simulate beef broth was prepared by dissolving the following ingredients in 2 l water:

| | |
|---|---|
| 1.00 | g of sodium lactate |
| 0.05 | g of inosine-5' monophosphate |
| 0.04 | g of of succinic acid |
| 2.00 | g of monosodium glutamate |
| 2.00 | g of caseine hydrolysate |
| 0.05 | g of tartaric acid |
| 0.025 | g of creatine |
| 13.0 | g of sodium chloride. |

The solution obtained was divided into two equal volumes and to one of these solutions 300 mg of calcium-5-ketogluconate.3aq was added. Both solutions were brought at pH=5.8 and heated to the boil for 10 minutes. Subsequently they were evaluated blind in a triangle test by a panel of 12 experienced tasters. The result was that 11 out of 12 panelists preferred the mixture with the calcium-5-ketogluconate, as this showed the better beef broth character with respect to odour and taste.

When the test was repeated, but this time with addition of 1000 mg of calcium-5-ketogluconate instead of 300 mg, the sample with the calcium-5-ketogluconate was preferred by 9 out of 12 panellists as regards odour, and by 8 out of 12 panellists as regards taste.

EXAMPLE 15

100 mg of calcium-5-ketogluconate.3aq were dissolved in 1 l water, after which 50 g of the following dry soup mix were added to the solution thus obtained:

| | |
|---|---|
| 90 | g of sodium chloride |
| 20 | g of monosodium glutamate |
| 50 | g of beef suet |
| 200 | g of vermicelli |
| 20 | g of caseine hydrolysate |
| 30 | g of dried onions |
| 10 | g of dried carrots |
| 2 | g of herb mix. |

The total composition was boiled for 20 minutes. The reference sample was prepared by dissolving 50 g of the above mix in 1 l water and boiling this for 20 minutes. The two samples were evaluated blind in a triangle test by a panel of 12 persons, 9 of whom preferred the soup with the calcium-5-ketogluconate.

EXAMPLE 16

A sauce was prepared by adding 10.4 g of the following mix in 200 ml water:

| | |
|---|---|
| 6 | g of sodium chloride |
| 25 | g of milk powder |
| 10 | g of vegetable fat |
| 6 | g of soybean hydrolysate |
| 5 | g of monosodium glutamate |
| 0.125 | g of herb mix. |

To this sauce 60 mg of potassium-5-ketogluconate were added. As a reference sample 10.4 g of the above mixture were added to 200 ml water. The two mixtures were boiled for 3 minutes and then stored for 2 hours at 80° C. Subsequently odour and taste were evaluated blind in a triangle test by a panel of 12 experienced tasters. In this test 8 out of 12 panellists preferred the sauce containing the potassium-5-ketogluconate. Particularly the odour of the sauce with the 5-ketogluconate was judged as being fuller and meatier. From this Example it appears that the present invention has made it possible to heat foodstuffs for some considerable time without any loss in flavour quality.

EXAMPLE 17

A goulash was prepared from the following ingredients:

| | |
|---|---|
| 150 | g of cooked pork |
| 1 | g of meat extract paste |
| 20 | g of red wine |
| 10 | g of soybean hydrolysate |
| 50 | g of beef suet |
| 3 | g of monosodium glutamate |
| 6 | g of sodium chloride |
| 50 | g of red paprika |
| 50 | g of fried onions |
| 50 | g of mushrooms |
| 100 | g of tomatoes |
| 60 | g of flour |
| 0.400 | g of pepper |
| 0.080 | g of mace |
| 0.060 | g of thyme |
| 0.060 | g of cloves |
| 0.100 | g of laurel |
| 0.200 | g of coriander |
| 1.300 | g of celery. |

The mixture was filled up with water to 1 liter.

An identical mixture was prepared, to which however 300 mg of free 5-ketogluconic acid were added. Subsequently both mixtures were canned in 0.5 liter cans and sterilised in an autoclave (50 minutes at 120° C.). After cooling the cans were opened and the goulash was shortly heated before testing. Odour and taste were evaluated blind in a triangle-test by a panel of 12 experienced tasters. In this test 9 out of 12 panellists distinctly preferred the goulash with the 5-ketogluconic acid, particularly the taste being judged as fuller, stronger and meatier.

EXAMPLE 18

4.8 g (10 mmol) of calcium-5-ketogluconate,3aq were brought into powder form and suspended in 200 ml water to which 20 ml 1N sulphuric acid had been added. The suspension was heated with stirring at 70° C. for 1 hour, during which the calcium-5-ketogluconate slowly dissolves and the calcium sulphate formed slowly precipitates. The solution was cooled for 1 hour with stirring and then filtered. The filtrate obtained was reduced to an oil by evaporation, followed by shaking of the oil with 30 ml ethanol. The mixture obtained was filtered so as to entirely remove the calcium sulphate formed, after which the filtrate was reduced by evaporation to form a colourless oil of the free 5-ketogluconic acid. The oil obtained was neutralized with 20 ml 1N sodium hydroxide, after which 1.11 g of cysteine. HCl.H$_2$O was added and the mixture thus obtained was brought to a pH=4.5 by adding concentrated sodium hydroxide. The mixture of pH=4.5 was heated for 2.5 h on an oil bath of 140° C., after which 21 g of maltodextrin were added to the mixture and the so obtained slurry was spray-dried. A white powder was obtained having a strong flavour of roasted beef without unpleasant notes.

I claim:

1. A process for preparing 4-hydroxy-5-methyl-2,3-dihydrofuranone-3, which comprises heating a solution of a 5-keto-aldohexonic acid or a derivative thereof in a polar solvent at a pH value between 1 and 7 to a temperature of 70° C. to 150° C.

2. A process according to claim 1, wherein the pH value lies between about 2 and about 7.

3. A process according to claim 1, wherein the solution is heated to a temperature between 95° C. and 110° C.

4. A process according to claim 3, wherein the solution is heated to a temperature between 100° C. and 105° C.

5. A process according to claim 1, wherein the polar solvent is selected from the group consisting of methanol, ethanol, water and mixtures thereof.

6. A process according to claim 1, wherein the 5-keto-aldohexonic acid or a derivative thereof is selected from the group consisting of 5-ketogluconic acid, D-arabino-5-hexulosonic acid and derivatives thereof which comprise organic salts, inorganic salts and lower alkyl esters of said acids.

7. A process for changing the organoleptic properties of a foodstuff or an ingredient for a foodstuff which before consumption has a pH value between 5 and 7 and which has to be heated for at least 15 minutes at a temperature of at least 70° C., characterized in that from 30 ppm to 2000 ppm, calculated on the weight of the foodstuff or the ingredient for the foodstuff, of a 5-keto-aldohexonic acid or its derivative, calculated as the acid, are incorporated into the foodstuff or the ingredient therefor.

8. A process according to claim 7, characterized in that from 100 ppm to 300 ppm, calculated on the weight of the foodstuff or the ingredient therefor, of the 5-keto-aldohexonic acid or its derivative, calculated as the acid, are incorporated into the foodstuff or the ingredient therefor.

9. A process according to claims 7 or 8, characterized in that a hydrogen sulphide donor is also incorporated into the foodstuff or the ingredient therefor.

10. A process according to claim 9, characterized in that the hydrogen sulphide donor is selected from the group consisting of cysteine and the sulphides or hydrosulphides of an alkali metal, an alkaline earth metal or ammonia.

11. A process according to claims 7, 8, 9 or 10, characterized in that the 5-keto-aldohexonic acid or its derivative is selected from the group consisting of 5-ketogluconic acid, D-arabino-5-hexulosonic acid, the edible organic salts thereof, the edible inorganic salts thereof, and the lower alkyl esters thereof.

12. A process according to claim 1, wherein said process is conducted in the presence of a hydrogen sulfide donor.

13. A process according to claim 12, wherein the hydrogen sulfide donor is selected from the group consisting of cysteine, sulphides of an alkali metal, hydrosulphides of an alkali metal, sulphides of an alkaline earth metal, hydrosulphides of an alkaline earth metal, ammonium sulphide and ammonium hydrosulphide.

* * * * *